United States Patent [19]

Tanaka et al.

[11] Patent Number: 5,756,842
[45] Date of Patent: May 26, 1998

[54] PROCESS FOR PREPARING LACTAMIDE

[75] Inventors: Fumio Tanaka; Tsumoru Morimoto; Takako Uchiyama; Takafumi Abe, all of Niigata, Japan

[73] Assignee: Mitsubishi Gas Chemical Company, Inc., Tokyo, Japan

[21] Appl. No.: 729,385

[22] Filed: Oct. 11, 1996

[30] Foreign Application Priority Data

Nov. 7, 1995 [JP] Japan ................................. 7-288244

[51] Int. Cl.$^6$ ................................................ C07C 231/06
[52] U.S. Cl. ........................... 564/126; 564/125; 564/130
[58] Field of Search ................................. 564/125, 126, 564/130

[56] References Cited

U.S. PATENT DOCUMENTS 4,018,829  4/1977  Gruber et al. ............................ 564/126
5,175,366  12/1992 Ebata et al. ............................. 564/126

FOREIGN PATENT DOCUMENTS

| 0777208   | 1/1968  | Canada .................................. 564/130 |
| 0 379 111 | 7/1990  | European Pat. Off. . |
| 0 412 310 | 2/1991  | European Pat. Off. . |
| 0 461 850 | 12/1991 | European Pat. Off. . |
| 0 597 298 | 5/1994  | European Pat. Off. . |

*Primary Examiner*—Shailendra Kumar
*Attorney, Agent, or Firm*—Frishauf, Holtz, Goodman, Langer & Chick, P.C.

[57] ABSTRACT

There is herein disclosed a process for preparing a lactamide by hydrating lactonitrile in the presence of a catalyst mainly comprising a manganese oxide, and a nitrogen-containing compound such as ammonia or diethylamine. According to this process, the lactamide can be obtained from lactonitrile in a high yield, while the high activity of the catalyst is maintained for a long period of time.

14 Claims, No Drawings

PROCESS FOR PREPARING LACTAMIDE

BACKGROUND OF THE INVENTION

1. Field of the Invention

The present invention relates to a process for preparing a lactamide, and more specifically, it relates to a process for preparing a lactamide by the liquid phase hydration reaction of lactonitrile. A lactamide is a material for use in the manufacture of a lactic acid ester by reactions with a formic acid ester or an alcohol. It is also possible to manufacture lactic acid by the further hydrolysis reaction of this lactic acid ester. Needless to say, the lactic acid ester and lactic acid are useful as materials or solvents for organic synthesis, and in particular, lactic acid is useful as a material for a fungicide or a biodegradable polymer. In addition, the lactic acid ester can be used as a material in manufacturing an acrylic acid ester by dehydration reaction, and it is industrially important and can be applied for use for many purposes.

2. Description of the Related Arts

As a catalyst which can be used in the case that the hydration reaction of a nitrile is carried out to prepare a corresponding carboxylic acid amide, German Patent No. 2131813 has disclosed the employment of manganese dioxide. Furthermore, in U.S. Pat. No. 4,018,829, it has been described that δ type manganese dioxide is used as a catalyst in the hydration reaction of acetocyanohydrin.

In addition, Japanese Patent Publication No. 47822/1986 and U.S. Pat. No. 5175366 have disclosed that a manganese dioxide catalyst is used in the hydration reaction of lactonitrile in a cyanohydrin group in which acetocyanohydrin is included. In Japanese Patent Application Laid-open Nos. 57534/1988 and 57535/1988, a technique of adding zinc and a technique of reducing potassium permanganate with hydrochloric acid have been disclosed as methods for preparing the manganese dioxide catalyst.

However, when manganese dioxide obtained by each of the above-mentioned techniques is directly used as the catalyst for the hydration reaction of lactonitrile, its catalytic activity is not sufficient, and in consequence, some problems are present. For example, the catalyst must be used in large quantities, the yield of the desired lactamide is low, and the catalytic activity promptly deteriorates in a relatively short period of time. For these reasons, the above-mentioned techniques have not been put into practical use so far.

SUMMARY OF THE INVENTION

An object of the present invention is to provide an industrially useful process for preparing a lactamide which can solve the above-mentioned problems of conventional techniques.

The present inventors have found that the activity of a manganese dioxide catalyst is closely concerned with a zirconium element, a vanadium element, a tin element and an alkaline metal element which coexist in the catalyst, and the rapid deterioration of the catalytic activity can also be inhibited by adding any of these elements. In addition, it has also been found that the poisonous function, against the catalyst, of free carboxylic acids secondarily produced in a main reaction system can be inhibited by ammonia or a specific amine compound. The present invention has been completed on the basis of such findings. That is to say, the present invention provides a process for preparing a lactamide which comprises hydrating lactonitrile in the presence of a catalyst containing a manganese oxide as a main component and a nitrogen-containing compound represented by the general formula (I)

wherein $R^1$ to $R^3$ are each a hydrogen atom or an atomic group having 1 to 8 carbon atoms.

DESCRIPTION OF THE PREFERRED EMBODIMENTS

A process of the present invention will be described in more detail.

Lactonitrile which can be used in the present invention can be obtained by various methods, and for example, it can easily be manufactured from acetaldehyde and hydrogen cyanide in the presence of a basic catalyst.

Furthermore, as catalysts mainly comprising a manganese oxide which can be used in the process of the present invention, various kinds of catalysts are applicable. Preferable examples of the catalysts include (1) a modified manganese dioxide containing an alkaline metal element (particularly, a sodium element or a potassium element) and (2) a modified manganese dioxide catalyst containing an alkaline metal element and at least one element selected from the group consisting of a zirconium element, a vanadium element and a tin element. In this case, no particular restriction is put on the content of each element, but preferably, the content of at least one element selected from the group consisting of the zirconium element, the vanadium element and the tin element is in the range of 0.005 to 0.1 in terms of its atomic ratio to the manganese element, and the content of the alkaline metal element is in the range of 0.05 to 0.5 in terms of its atomic ratio to the manganese element.

The catalyst containing a manganese oxide as a main component, particularly the manganese dioxide catalyst which can be used in the present invention can be prepared as follows.

It has been described hereinbefore that manganese dioxide can be used in the hydration reaction of cyanohydrin, but manganese dioxide is a manganese oxide present between $MnO_{1.7}$ and $MnO_2$, and as its crystalline structure, α type, β type, γ type, ε type and the like are known. In addition, since manganese dioxide transfers between the respective phases and its crystallinity changes, the structure of manganese dioxide is extremely complex and unsettled. Manganese dioxide is also present in nature, but in the case that it is used as the catalyst, manganese dioxide obtained by each one or a combination of a method which comprises oxidizing divalent manganese and another method which comprises reducing heptavalent manganese is suitable. For example, there are known a method which comprises reducing a permanganate compound at 20° to 100° C. in a neutral or an alkaline range [Zeit. Anorg. Allg. Chem., Vol. 309, p. 1 to 32 and p. 121 to 150 (1961)], a method which comprises treating potassium permanganate and manganese sulfate in an acidic state [J. Chem. Soc., Vol. 1953, p. 2189 (1953)], a method which comprises reducing a permanganate with a hydrohalogenic acid (Japanese Patent Application Laid-open No. 57535/1988), and a method which comprises electrolytically oxidizing an aqueous manganese sulfate solution. However, it is preferable to simultaneously use divalent manganese and heptavalent manganese, because this usage makes it possible to control a crystalline type, the size of a specific surface area, and a kind and amount of alkaline metal.

As a divalent manganese source which can be used in the preparation of the above-mentioned catalyst, a water-soluble salt can be selected, and above all, a sulfate is particularly preferable. As a heptavalent manganese source, water-soluble potassium permanganate or sodium permanganate is particularly preferable. As the manganese dioxide catalyst of the present invention, a modified manganese dioxide containing an alkaline metal element is preferable, as described above. Moreover, a modified manganese dioxide containing an alkaline metal element and at least one element selected from the group consisting of a zirconium element, a vanadium element and a tin element is preferable.

In order to introduce the alkaline metal element and the zirconium element, the vanadium element and/or the tin element into manganese dioxide, a technique such as impregnation, adsorption, kneading or coprecipitation can be used. However, for the sake of the uniform mixing of these elements with manganese dioxide, the coprecipitation method is particularly preferable. The preparation of the manganese dioxide catalyst can be done under either of acidic conditions and basic conditions, but the preparation under the acidic conditions is more preferable. If the preparation is carried out under the basic conditions, it is suitable that prior to reaction, manganese dioxide is washed with dilute sulfuric acid or the like.

That is to say, a water-soluble divalent manganese salt and at least one compound selected from the group consisting of water-soluble salts of zirconium, vanadium and tin are dissolved in water, and the resulting solution is then poured into an aqueous heptavalent manganese (potassium permanganate or sodium permanganate) solution, followed by mixing. Next, the resulting precipitate is collected by filtration, washed, and then dried to prepare the desired catalyst. The coprecipitation is carried out under atmospheric pressure or an increased pressure at a temperature in the range of 30° to 250° C., preferably 50° to 200° C. If the temperature is lower than this range, the yield of manganese dioxide is low and the content of the alkaline metal is also low, because the reactivity of divalent manganese with heptavalent manganese is low. If the temperature is higher than the above-mentioned range, the surface area of manganese dioxide unpreferably reduces. As materials of the elements which are to be introduced into manganese dioxide, salts, hydroxides, oxides or simple substances of the metallic elements can be used, but water-soluble salts are usually selected and above all, sulfates are particularly preferable.

In the present invention, a formed article of the modified manganese dioxide prepared as described above can be used as a fixed bed catalyst, or alternatively powder, granules or fine spheres of the modified manganese dioxide can be used as a slurry catalyst for the hydration reaction of lactonitrile in a batch type or a continuous type reactor. The hydration reaction, in which the modified manganese dioxide catalyst of the present invention is used, can usually be carried out in a system containing an excessive amount of water. That is to say, a concentration of lactonitrile in a material solution (containing lactonitrile and water as main components) is in the range of 5 to 60% by weight, preferably 10 to 50% by weight. A reaction temperature is in the range of 20° to 120° C., preferably 30° to 90° C. If the reaction temperature is lower than this range, a reaction rate is low, and if it is higher than the range, by-products formed by the decomposition of lactonitrile increase unpreferably.

Furthermore, usually 0.0001 to 5% by weight, preferably 0.0005 to 3% by weight of a nitrogen-containing compound represented by the general formula (I) is added to the reaction material containing lactonitrile and water as the main components, whereby the activity of the catalyst can be improved and the deterioration of the activity with time can remarkably be inhibited, and a high lactamide yield can be obtained, while the high activity of the catalyst is maintained.

In this general formula (I), $R^1$ to $R^3$ are each a hydrogen atom or an atomic group having 1 to 8 carbon atoms. Preferable examples of this atomic group having 1 to 8 carbon atoms include an alkyl group having 1 to 8 carbon atoms, a cycloalkyl group having 3 to 8 carbon atoms, a hydroxyalkyl group having 1 to 8 carbon atoms, an aminoalkyl group having 1 to 8 carbon atoms and a halogenoalkyl group having 1 to 8 carbon atoms. In addition, typical examples of the nitrogen-containing compound represented by the general formula (I) include ammonia, monoethylamine, diethylamine, triethylamine, monomethylamine, dimethylamine, trimethylamine, monopropylamine, dipropylamine, tripropylamine, monoisopropylamine, diisopropylamine, triisopropylamine, monoethanolamine, diethanolamine, triethanolamine, ethylenediamine and diethylenetriamine. They can be used singly or in a combination of two or more thereof.

According to the process of the present invention, the lactamide can be obtained from lactonitrile in a high yield, while the high activity of the catalyst is maintained for a long period of time, and therefore it has an industrially extremely large significance.

Next, the process of the present invention will be described in more detail in accordance with examples and comparative examples, but the scope of the present invention should not be limited to these examples.

COMPARATIVE EXAMPLE 1

Preparation of a catalyst: A solution obtained by mixing 178.5 g of an aqueous manganese sulfate solution (containing 11% of Mn), 10.0 g of concentrated sulfuric acid and 25 g of water was promptly poured at 70° C. with stirring into a solution obtained by dissolving 56.4 g of potassium permanganate in 560 g of water. The stirring was further continued, and aging was then carried out at 90° C. for 3 hours, and the resulting precipitate was collected by filtration, and then washed 4 times with 1000 g of water. Next, the obtained cake was dried at 110° C. overnight to obtain 64.2 g of a modified manganese dioxide. The contents of metallic components in the thus obtained compound were measured, and as a result, it was apparent that an atomic ratio of potassium/manganese was 0.09/1.00.

Reaction: Manganese dioxide obtained above was crushed so as to be a size of 10 to 20 mesh, and 3.5 g of the thus ground manganese dioxide was filled into a glass reaction tube having an inner diameter of 10 mm equipped with a jacket. Through this jacket, warm water at 40° C. was circulated. Next, a raw material solution prepared by mixing 20 parts by weight of lactonitrile and 80 parts by weight of water was fed to the reaction tube at a flow rate of 6.2 g/hr. The solution discharged from the reactor was fed to the reaction again through its inlet at a flow rate 31 g/hr (circulation ratio=5) by a circulating pump. For the reaction solution overflowed from a liquid tank in the lower portion of the reactor, its composition was analyzed after 24 hours and 14 days from the start of the reaction by a high performance liquid chromatography. As a result, the conversions of lactonitrile after 24 hours and 14 days were 81% and 71%, respectively, and the selectivities (based on lactonitrile) of a lactamide after 24 hours and 14 days were similarly 94%. In addition, trace amounts of lactic acid, acetaldehyde and acetic acid were detected.

EXAMPLES 1 AND 2

Preparation of a catalyst: The same procedure as in Comparative Example 1 was carried out.

Reaction: The hydration reaction of lactonitrile was carried out in the presence of 3.5 g of the manganese dioxide catalyst obtained above in the same manner as in Comparative Example 1 except that ammonia was used as an additive in Example 1 and diethylamine as an additive in Example 2, though any ammonia was not added to a feed material in Comparative Example 1. In Example 1, the amount of ammonia was 0.2% by weight based on the weight of the raw material solution, and in Example 2, the amount of diethylamine was 0.86% by weight based on the weight of the material solution. The reaction was carried out under the same reaction conditions as in Comparative Example 1. Table 1 shows the conversions of lactonitrile after 24 hours and 14 days. Furthermore, the selectivities of a lactamide after 24 hours and 14 days were similarly 95% in both Example 1 and Example 2.

TABLE 1

| | Conversion of Lactonitrile (%) | |
| --- | --- | --- |
| | After 24 hours | After 14 days |
| Comp. Example 1 | 81.0 | 71.0 |
| Example 1 | 87.9 | 86.3 |
| Example 2 | 90.2 | 90.1 |

COMPARATIVE EXAMPLE 2

Preparation of a catalyst: A solution obtained by mixing 138.7 g of an aqueous manganese sulfate solution (containing 11% of Mn), 2.91 g of stannous sulfate, 23.9 g of concentrated sulfuric acid and 20 g of water was promptly poured at 70° C. with stirring into a solution obtained by dissolving 66.4 g of potassium permanganate in 580 g of water. The stirring was further continued, and aging was then carried out at 90° C. for 3 hours, and the resulting precipitate was collected by filtration, and then washed 4 times with 1000 g of water. Next, the obtained cake was dried at 110° C. overnight to obtain 68.2 g of a modified manganese dioxide. The contents of metallic components in the thus obtained compound were measured, and as a result, it was apparent that an atomic ratio of tin/potassium/ manganese was 0.02/0.09/1.00.

Reaction: Reaction was carried out in the presence of 3.5 g of the manganese dioxide catalyst obtained above in the same manner as in Comparative Example 1 except that the flow rate of a material solution was 7 g/hr and a circulation ratio was 10. As a result, the conversions of a lactamide after 24 hours and 14 days were 83.4% and 76.5%, respectively, and the selectivities of a lactamide after 24 hours and 14 days were similarly 95%.

EXAMPLES 3 AND 4

Preparation of a catalyst: The same procedure as in Comparative Example 2 was carried out.

Reaction: The hydration reaction of lactonitrile was carried out in the presence of 3.5 g of the manganese dioxide catalyst obtained above in the same manner as in Comparative Example 2 except that ammonia was used as an additive in an amount of 0.2% by weight based on the weight of a material solution in Example 3 and diethylamine was used as an additive in an amount of 0.86% by weight based on the weight of the material solution in Example 4. Table 2 shows the conversions of lactonitrile after 24 hours and 14 days. Furthermore, the selectivities of a lactamide after 24 hours and 14 days were similarly 95%.

TABLE 2

| | Conversion of Lactonitrile (%) | |
| --- | --- | --- |
| | After 24 hours | After 14 days |
| Comp. Example 2 | 83.4 | 76.4 |
| Example 3 | 89.8 | 86.6 |
| Example 4 | 91.3 | 91.0 |

EXAMPLE 5

Preparation of a catalyst: The same procedure as in Comparative Example 2 was repeated except that the amount of an aqueous manganese sulfate solution (containing 11% of Mn) was 117.7 g and that of stannous sulfate was 11.6 g, thereby obtaining 72.2 g of a modified manganese dioxide. The contents of metallic components in the thus obtained compound were measured, and as a result, it was apparent that an atomic ratio of tin/potassium/ manganese was 0.078/0.08/1.00.

Reaction: The hydration reaction of lactonitrile was carried out in the presence of 3.5 g of the manganese dioxide catalyst obtained above in the same manner as in Comparative Example 2 except that triethylamine was used as an additive in an amount of 0.86% by weight based on the weight of a material solution. As a result, the conversions of lactonitrile after 24 hours and 14 days were 91.5% and 91.3%, respectively. Furthermore, the selectivities of a lactamide after 24 hours and 14 days were similarly 95%.

EXAMPLE 6

Preparation of a catalyst: The same procedure as in Comparative Example 2 was repeated except that stannous sulfate was replaced with 2.20 g of vanadyl sulfate, thereby obtaining 67.5 g of a modified manganese dioxide. The contents of metallic components in the thus obtained compound were measured, and as a result, it was apparent that an atomic ratio of vanadium/potassium/manganese was 0.02/0.09/1.00.

Reaction: The hydration reaction of lactonitrile was carried out in the same manner as in Example 4 except that 3.5 g of the manganese dioxide catalyst obtained above was used. As a result, the conversions of lactonitrile after 24 hours and 14 days were 92.3% and 92.2%, respectively, and the selectivities of a lactamide after 24 hours and 14 days were similarly 95%.

EXAMPLE 7

Preparation of a catalyst: The same procedure as in Comparative Example 2 was repeated except that stannous sulfate was replaced with 4.80 g of zirconium sulfates. tetrahydrate, thereby obtaining 69.8 g of a modified manganese dioxide. The contents of metallic components in the thus obtained compound were measured, and as a result, it was apparent that an atomic ratio of zirconium/potassium/ manganese was 0.018/0.10/1.00.

Reaction: The hydration reaction of lactonitrile was carried out in the same manner as in Example 4 except that 3.5 g of the manganese dioxide catalyst obtained above was used. As a result, the conversions of lactonitrile after 24 hours and 14 days were 91.5% and 91.3%, respectively, and the selectivities of a lactamide after 24 hours and 14 days were 95% and 94%, respectively.

EXAMPLE 8

Preparation of a catalyst: A solution obtained by mixing 138.7 g of an aqueous manganese sulfate solution (containing 11% of Mn), 1.46 g of stannous sulfate, 2.40 g of zirconium sulfate.tetrahydrate, 23.9 g of concentrated sulfuric acid and 20 g of water was promptly poured at 70° C. with stirring into a solution obtained by dissolving 66.4 g of potassium permanganate in 580 g of water. The stirring was further continued, and aging was then carried out at 90° C. for 3 hours, and the resulting precipitate was collected by filtration, and then washed 4 times with 1000 g of water. Next, the obtained cake was dried at 110° C. overnight to obtain 68.9 g of a modified manganese dioxide. The contents of metallic components in the thus obtained compound were measured, and as a result, it was apparent that an atomic ratio of tin/zirconium/potassium/manganese was 0.01/0.008/0.10/1.00.

Reaction: The hydration reaction of lactonitrile was carried out in the same manner as in Example 4 except that 3.5 g of the manganese dioxide catalyst obtained above was used. As a result, the conversions of lactonitrile after 24 hours and 14 days were 92.0% and 91.8%, respectively, and the selectivities of a lactamide after 24 hours and 14 days were similarly 95%.

EXAMPLE 9

Preparation of a catalyst: The same procedure as in Comparative Example 2 was repeated except that potassium permanganate was replaced with 70.5 g of sodium permanganate.trihydrate, thereby obtaining 66.5 g of a modified manganese dioxide as a catalyst. The contents of metallic components in the thus obtained compound were measured, and as a result, it was apparent that an atomic ratio of tin/sodium/manganese was 0.02/0.08/1.00.

Reaction: The hydration reaction of lactonitrile was carried out in the same manner as in Example 4 except that 3.5 g of manganese dioxide catalyst obtained above was used. As a result, the conversions of lactonitrile after 24 hours and 14 days were 90.5% and 90.4%, respectively, and the selectivities of a lactamide after 24 hours and 14 days were similarly 94%.

What is claimed is:

1. A process for preparing a lactamide which comprises hydrating lactonitrile in the presence of a catalyst containing a manganese oxide as a main component and a nitrogen-containing compound represented by the formula (I)

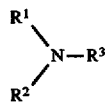

wherein $R^1$ to $R^3$ are each a hydrogen atom, an alkyl group having 1 to 8 carbon atoms, a cycloalkyl group having 3 to 8 carbon atoms, a hydroxyalkyl group having 1 to 8 carbon atoms, an aminoalkyl group having 1 to 8 carbon atoms or a halogenalkyl group having 1 to 8 carbon atoms.

2. The process according to claim 1 wherein the catalyst containing the manganese oxide as the main component is a modified manganese dioxide containing an alkaline metal element.

3. The process according to claim 1 wherein the catalyst containing the manganese oxide as the main component is a modified manganese dioxide containing an alkaline metal element and at least one element selected from the group consisting of a zirconium element, a vanadium element and a tin element.

4. The process according to claim 2 wherein the catalyst containing the manganese oxide as the main component is manganese dioxide containing at least one element selected from the group consisting of a sodium element and a potassium element.

5. The process according to claim 3 wherein an atomic ratio, to a manganese element, of at least one element selected from the group consisting of the zirconium element, the vanadium element and the tin element is in the range of 0.005 to 0.1.

6. The process according to claim 4 wherein an atomic ratio, to a manganese element, of at least one element selected from the group consisting of a sodium element and a potassium element is in the range of 0.05 to 0.5.

7. The process according to claim 1 wherein the nitrogen-containing compound represented by the formula (I) is ammonia, monoethylamine, diethylamine, triethylamine, monomethylamine, dimethylamine, trimethylamine, monopropylamine, dipropylamine, tripropylamine, monoisopropylamine, diisopropylamine, triisopropylamine, monoethanolamine, diethanolamine, triethanolamine, ethylenediamine or diethylenetriamine.

8. The process according to claim 1 wherein the amount of the nitrogen-containing compound represented by the formula (I) is in the range of 0.0001 to 5% by weight with respect to a reaction material containing lactonitrile and water as main components.

9. The process according to claim 1 wherein the lactonitrile is in a concentration in a material solution containing lactonitrile and water of 5 to 60 weight %.

10. The process according to claim 9 wherein the lactonitrile is in a concentration of 10 to 50 weight % in the material solution.

11. The process according to claim 10 wherein the process is carried out at a temperature of 20° to 120° C.

12. The process according to claim 11 wherein the temperature is 30° to 90° C.

13. The process according to claim 12 wherein the nitrogen-containing compound is in an amount of 0.0005 to 3% by weight with respect to the material solution.

14. The process according to claim 13 wherein the nitrogen-containing compound is ammonia, monoethylamine, diethylamine, triethylamine, monomethylamine, dimethylamine, trimethylamine, monopropylamine, dipropylamine, tripropylamine, monoisopropylamine, diisopropylamine, triisopropylamine, monoethanolamine, diethanolamine, triethanolamine, ethylenediamine or diethylenetriamine.

* * * * *